United States Patent [19]

van den Berg et al.

[11] 4,130,903

[45] Dec. 26, 1978

[54] PROTECTIVE DEVICE PARTICULARLY FOR WELDING AND CUTTING WORK

[76] Inventors: Henrikus J. van den Berg; Gerardus C. A. M. Hurkmans, both c/o Techn. Bureau A.B.O.F. 1972 B.V., Joubertstr. 10-12, both of Nijmegen, Netherlands

[21] Appl. No.: 740,676

[22] Filed: Nov. 10, 1976

[30] Foreign Application Priority Data

Nov. 11, 1975 [DE] Fed. Rep. of Germany ....... 2550559

[51] Int. Cl.² .............................................. A61F 9/06
[52] U.S. Cl. ............................................. 2/8; 2/433
[58] Field of Search ................ 2/8, 432, 433; 351/4 G

[56] References Cited

U.S. PATENT DOCUMENTS

| 1,959,915 | 5/1934 | Guthrie | 2/433 X |
| 2,232,455 | 2/1941 | Hebrard | 351/46 |
| 3,238,535 | 3/1966 | Richey | 2/8 |
| 3,873,804 | 3/1975 | Gordon | 2/8 |
| 3,943,573 | 3/1976 | Budmiger | 2/8 |

FOREIGN PATENT DOCUMENTS

| 0572158 | 3/1933 | Fed. Rep. of Germany | 2/8 |
| 2315308 | 10/1973 | Fed. Rep. of Germany | 2/8 |

Primary Examiner—Peter Nerbun
Attorney, Agent, or Firm—Cushman, Darby & Cushman

[57] ABSTRACT

The present invention relates to a protective device for performing work in areas of greatly varying light intensities, comprising a viewing window having a portion provided with a pair of relatively adjustable grid supports with the movement of said supports being adapted to be controlled by electromagnetic means in response to the intensity of light incident on said protective device and/or the type of light, and which allow the affected portion of said viewing window to be darkened (dimmed) or rendered translucent, whereby said grid supports comprise a material being permeable to light in the visible range of spectrum and said darkening portions (the grid strips) comprise a material being highly absorbent to light in the visible range of spectrum. In a particular embodiment, the protective or safety device serves as a protective hood or helmut on as a protective shield for performing protective welding work; corresponding modification, however, this device may be used also in foundries, rolling mills, physical laboratories and similar facilities where the human eye must be protected against excessive intensities of light.

16 Claims, 6 Drawing Figures

PROTECTIVE DEVICE PARTICULARLY FOR WELDING AND CUTTING WORK

BACKGROUND OF THE INVENTION

There is known a protective hood or helmet including protective windows (safety glasses) and contemplated to be used for performing welding, cutting and similar work (German Pat. No. 572,153), which helmet comprises a twopiece protective window the lower portion of which is made of an almost opaque material inhibiting or absorbing harmful radiation, and of an upper transparent viewing portion being formed as a grid adapted to be opened and closed. Opening and closing of the grid is effected by a small electromagnet or solenoid which is operated in response of the current passing through the welding or cutting torch.

It is also known (British Pat. No. 834,021) to provide a grid assembly comprising a stationary and a movable grid support each, whereby the movable support is adapted to be moved to and fro in front of the stationary support by an electromagnetic assembly against a spring bias, and adapted to be shifted by a specific distance in correspondence with the desired intensity of the light falling there through.

It has been found to be impossible to combine these conventional devices so as to to provide a universally useful protective device which is of light weight in operation and which may be manufactured at low cost. Especially, the conventional devices do not provide a cutting-off time lower than 1 ms. this short time rendering a real protection for the eyes. Generally, it is of disadvantage for the universal application that the protective device must be connected to the circuit of the welding apparatus. Particularly if a plurality of persons are present when a welding operation is carried out (training of apprentices!), it is not possible to connect all of their protective devices to the limited number of terminal jacks. Besides, so-called welding cabs are known where the operations are to be observed by third persons from the exterior. This construction, too, would require substantial technical expenditure in order to make the necessary connection. Furthermore, when the protective device is used in foundries and rolling mills, there is not present any electric circuit at all to which the protective device could be connected.

Accordingly, it is the object of the present invention to provide a protective device which may be employed in as universal a manner as possible for every work involving greatly varying intensities of light, which device should lend itself to inexpensive production and easy manufacture, and which device should be comfortable in use. Also, a particularly compact construction of the optical components should be possible, such that these components are easy to replace.

In a protective device of the kind as outlined at the beginning, these objects are solved in that photoelectric elements are provided adjacent said viewing window, said elements being adapted to produce a control signal equal to the intensity of light incident on said protective device and activating a control circuit for operating electromagnetic control elements. Accordingly, the invention departs from the principle of providing an exterior source for controlling the grid. Rather, the invention proposes to initiate the control in the region of the viewing window per se, whereby, for example, phototransistors, photocells and the like may be mounted to the edge of the window per se or immediately adjacent thereto at the protective device as such.

Furthermore, it is proposed to provide a logic circuit including a Darlington transistor pair or couple which in the presence of a control signal of the light-sensitive elements corresponding to a high intensity of light, supplies current to a first magnet coil, and which in the presence of a control signal corresponding to a low intensity of light drives a second magnet coil, whereby control elements for shifting the grid supports are drawn to and fro between the coils. This electromechanical connection allows to exert sufficient power for shifting the grids, whereby only a relatively small rate of movement is required in order to align the grids with each other. Preferably, spacers disposed between the grid supports are additionally provided, which spacers reduce the frictional drag and substantially fully eliminate wear of the grid strips by rubbing against each other. Also, it is suggested that the width of the grid strip surface, plus the viewing strips or bars, is less than 2 mm, such that a small amount of movement only is necessary. In order that the sensitivity of the optical-electronic portion of the protective device may easily and automatically be matched to the ambient light intensity, a light-sensitive series resistor is coupled to the logic control circuit, which resistor responds to the ambient light only and sets the sensitivity of the logic circuit to various levels.

Preferably, the magnet coils are provided with yokes of a magnetic material, which yokes exhibit remanence or residual magnetism upon the termination of the current flow therethrough, such that a control element for shifting the grid supports remains in the respective shifted position reached at that moment. By this structure, pulsating or intermittent operation becomes possible.

If integrated circuits and transistors will be used, which only consume energy during the switching action, for operation only a 9 V — baby cell is necessary, which will last 6 months. Also, so called solar cells could be used, which get their energy by the welding light itself.

Furthermore, the invention proposes that one of the two grid supports is securely connected to an armature being positioned for movement between the magnetic portions of a pair of magnet coils. With a correspondingly small spacing between the two magnet coils, positive switching or shifting of the grids can be obtained even with a small current pulse. Advantageously, the magnetic yokes of the magnet coils are arranged in such a way that a pair of U-shaped yokes oppose each other with their free legs. An armature provided with a plug-in slot is disposed between the yokes, with a coupling member, preferably made of non-conductive plastic material and connected to one of the grid supports, being adapted to be inserted into said slot.

To extend the field of application, it is contemplated that the viewing window, comprising the pair of grid supports and a coupling member for connection to the armature, is mounted as a unit within a frame adapted to be slipped on, so as to be exchangeable in accordance with the respective varying working conditions.

Under all working conditions, it is expedient that the support material and the grid strips act to filter out the invisible radiation in the fringe area of the visible light spectrum, or that the grid strips with respect to their filter effect are adapted to the E.W. (electric welding) Standards.

Finally, the present invention provides a replaceable viewing window to be used in protective hoods for welding and for other protective or safety devices, comprising a first stationary grid support mounted in a frame, and a second grid support movable relative to said first grid support, whereby said second grid support is provided with a coupling member for connection to a movable armature, which armature is secured directly to said protective hood together with the electric components of a logic control circuit. In this construction, the viewing window or glass can be readily replaced should it become damaged or when the light conditions vary. Furthermore, the viewing window may be provided with filters for the photoelectric elements such that, when the viewing window is changed, the characteristic of these elements is altered, too.

Further properties and advantages as well as details of the control means are explained below by referring to the enclosed drawings. In the FIGS:

FIG. 1 shows one embodiment of the invention in the form of a protective welding helmet or safety hood having a replaceable viewing window according to the invention;

FIGS. 2a, 2b schematically show the relatively adjustable grid supports;

DETAILED DESCRIPTION

Figure 2A:
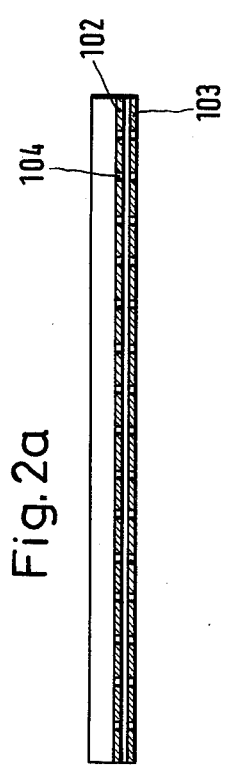
Figure 2B:
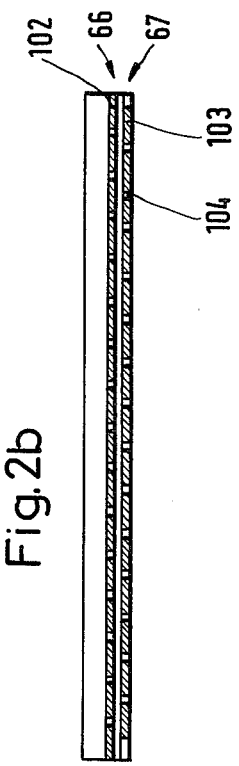
Figure 1:
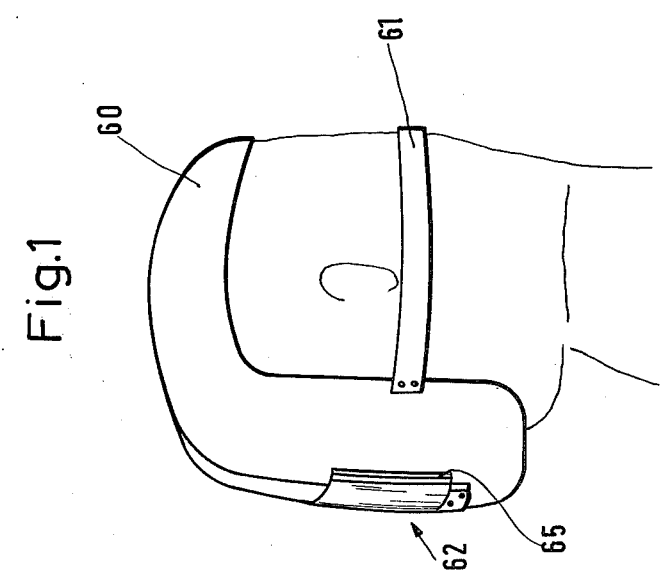

FIG. 1 illustrates a protective welding hood 60 comprising essentially a helmet-like portion, adapted to be fixed by means of a strap 61, and a replaceable viewing window 62. The viewing window 62 comprises an upper portion 63 and a lower portion 64 (FIG. 4) which portions are jointly arranged on a plastic plate or board. The plastic board is adapted to be moved up and down within guide rails 65 such that it may be removed from a position in front of the user's eyes. The upper portion 63 of the window 62 includes a pair of superimposed grids 66 and 67. The uppermost grid 67 has its corners securely connected to the board of the viewing window, whereas the lower (or rear) grid 66 is mounted for slight reciprocating movement relative to grid 67. FIGS. 2a and 2b show that the grids are formed of gaps 104 and strips 102, 103. When the strips are staggered relative to each other (FIG. 2b), the state of high light absorption is obtained. The grids per se are made of glass of of a transparent plastic material. The grid strips or lines, namely the substance highly absorbent to light, is applied thereto by printing, vapor deposition, etching or by means of a photographic process. On principle, each of these methods is suitable to apply a solid substance to a ceramic or other substrate.

The movable grid 66 has its lower edge portion securely connected to a block 50, serving as coupling member, through a projection. The block 50 terminates in a lug 42. This lug extends into an armature 40 made of iron and comprising a pair of jaws 45, 46 and a connector bolt. Lug 42 is inserted between the jaws in the manner of being inserted into a slot, and seated therein. The armature is retracted by a tension spring 47 together with the movable grid support, such that the latter is pressed against a guide rail 48.

The armature is movably mounted between the yokes 122, 134 of a pair of small magnet coils or solenoids 21, 33 through which current flows in dependence of the respectively desired switching or shift condition, so as to attract the armature towards the respective coil. At the same time, the end faces of the yokes act as contact faces 35, 36 (compare FIG. 3). The material of the yokes is iron which shows a certain remanence or residual magnetism when the current is cut off, such that the armature remains in its respectively last position in contact with one of the contact faces 35, 36. When the armature moves, block 50 is moved in combination with grid 66. The stroke of such movement (indicated by arrow a ... b) is just of such magnitude that the strips of the grid are aligned in the one position and precisely staggered (to fill the gaps) in the other position such that the obscured state is obtained.

In order to intensify the closing action of the magnet, and particularly to make sure that the grid support can positively close the grid supports when the battery becomes exhausted, a small spring 38 is attached to the armature 40 in such a fashion as to draw this armature in the closing direction together with the associated grid support. Thus, by means of this spring the armature is always pulled in the direction of the closed position even if the current is low, and even if the power flowing within the coil alone is not sufficient to withdraw the armature from the coil end.

Besides, for the case of failure of the battery current, measures are taken that the window is drawn into its closed position.

It is also possible (although not shown) to provide the coil 33 ("opener") with a second small winding which is constantly energized by a predetermined, low current causing coil 33 to act in such a way that the window is moved in the open position against the force of the spring. This small tension when the second winding is energized, does not affect the other switching or shifting operations. However, in the case of current breakdown, the window is drawn into the closed position for reasons of safety.

Figure 3:
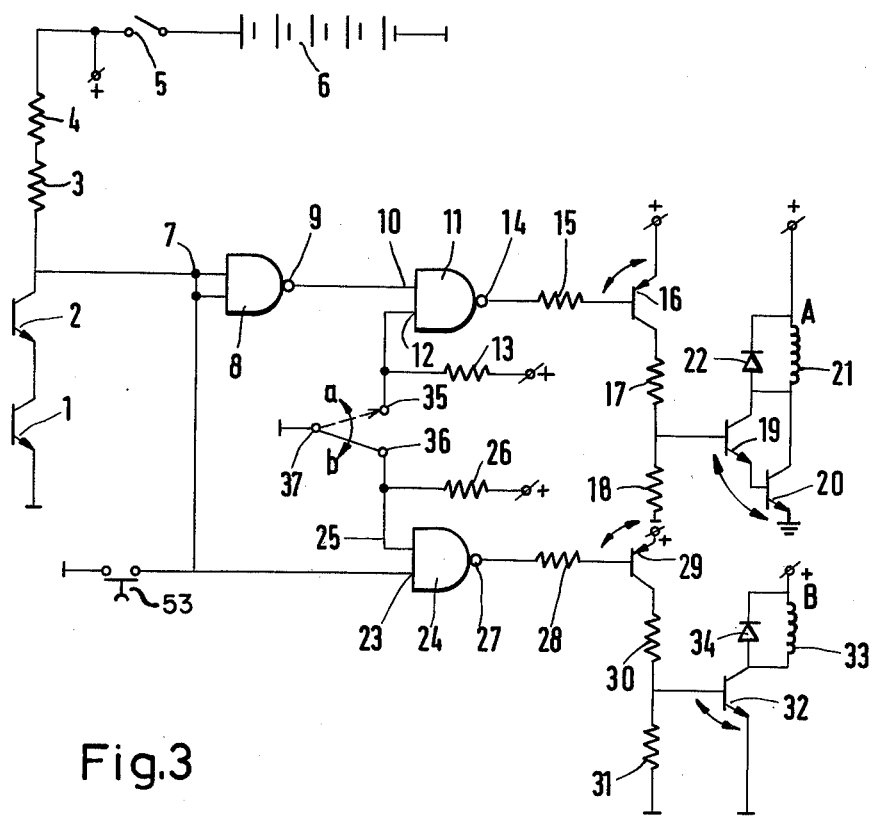
FIG. 3 is a diagram of a circuit for controlling the movement of the grid supports.

The contacts, coils and other movable and electronic components form part of a system cooperating with photoelectric elements which, in turn, are attached to the protective hood and serving to control the grid movement under varying light intensities. FIG. 3 shows a diagram of an electronic circuit arrangement suitable for this purpose. The arrangement includes a pair of series connected, light-sensitive or light-responsive transistors 1 and 2. Collector of transistor 2 is connected in series with a light-sensitive resistor 3, a resistor 4 and a switch 5 to the positive terminal of a D.C. source 6. Emitter of transistor 1 is grounded. Further, the collector of transistor 2 is connected to the two inputs 7 of a NAND gate 8, the output 9 of which is connected to the input 10 of another NAND gate 11. Input 12 of NAND gate 11 is connected to the positive terminal of a positive potential through a resistor 13. The output 14 of NAND gate 11 is applied to the base electrode of the transistor 16 through a resistor 15, with the emitter of said transistor being coupled to the positive potential and the collector thereof being grounded via the series connected resistors 17 and 18. The junction of resistors 17 and 18 is connected to the base of a pair of Darlington transistors 19 and 20 (in H connection mode). The emitter of transistor 20 is grounded, and both collectors are coupled to the positive potential through the parallel connection of an induction coil and a diode 22. Further, the collector of transistor 2 is connected to the input 23 of NAND gate 24 the input 25 of which is coupled to the positive potential through a resistor 26. One output 27 of this NAND gate is connected to the base of transistor 29 via the resistor 28. The emitter of transistor 29 is connected to the positive potential. The collector is grounded through the series connected resistors 30 and 31. The junction of resistors 30 and 31 is coupled to the base of transistor 32 (which may be a Darlington Pair) the emitter of which is grounded and the collector of which is coupled to the positive potential through a parallely connected coil 33 and diode 34. Also, input 12 of NAND gate 11 is connected to contact surface 35. The input 25 of NAND gate 24 is coupled to a fixed contact point 36 of switch 37 connecting one of the two contacts 35, 36 to ground potential. Coils 21 and 33 represent the magnet coils or windings of the pair of electromagnet yokes 122 and 134 which are shown in FIG. 4 with a common armature 40.

Figure 4:
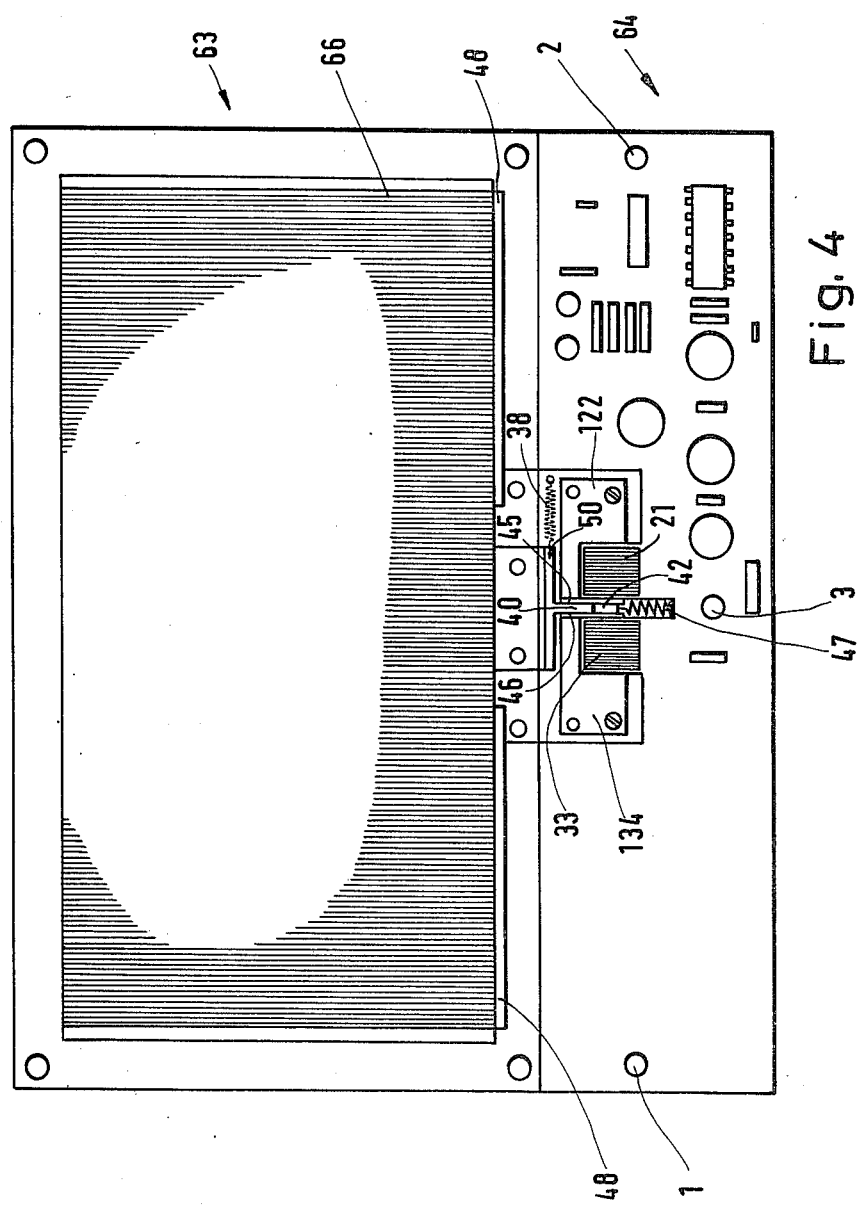
FIG. 4 is a plan view of a replaceable viewing window.

The function of the device is now described in detail by referring to FIGS. 3 and 4. As can be seen from FIG. 4, phototransistors 1 and 2 are inserted into separate jacks or sleeves and directed towards the light source. Therefore, these phototransistors are series connected to allow them to be positioned or oriented in such a manner that they are not influenced by other ambient light sources, if possible. It is suggested that the phototransistors be installed into small cups in such a manner that a funnel-shaped light incidence angle is produced, whereby these transistors respond to signals within this angle only while disturbing light from outside of this angular range is prevented from falling upon the phototransistors.

Furthermore, the collector line of phototransistors 1 and 2 includes a light-responsive LDR resistor 3. This resistor 3 functions to allow transistors 1 and 2 to be adjusted with respect to the ambient light automatically and as precisely as possible. Thus, this resistor is normally not affected by the light source actually to be detected; rather, it is irradiated by the ambient light only. Another resistor 4 limits the maximum current flowing through elements 1, 2 and 3.

Beginning with the normal state in which the grids are in their open conditions and the phototransistors 1 and 2 remain in the non-conducting state, these transistors always change into their conducting states as soon as light is incident upon them. Inputs 7 of NAND gates 8 are set to a logic ZERO condition, while output 9 is set to a logic ONE. Input 12 of NAND gate 11 is at a level ONE above resistor 13. Input 10 of NAND gate 11 becomes a logic ONE which causes output 14 to become a logic ZERO. In this way, transistors 16 and 19 and 20 become conductive. A current flows through coil 21 which attracts the armature and brings the movable grid 66 into the closed position. Further, rotation of the armature results in the switch lever 37 being moved into the vicinity of contact surface 35.

If at this point a contact is closed by abutment of the switch lever 37 against the contact surface, the input 12 becomes a logic ZERO and the output 14 a logic ONE, such that transistors 16, 19 and 20 become non-conductive so as to prevent current from flowing through coil 21. The lightpermeable system is now keptin the closed position by the remanence of coil 21.

When the light source becomes less intense, phototransistors 1 and 2 should take their non-conductive states. Input 23 of NAND gate 24 is supposed to become a logic ONE. Input 25 is at the level of a logic ONE by resistor 26, such that output 27 changes to ZERO. Transistors 29 and 32 become conductive, and current is allowed to flow through coil 33.

The magnetic field produced by coil 33 attracts the armature in a direction opposite to the direction of attraction of coil 21, whereby the movable grid shifts into an open condition. Further, the switch lever 37 is supposed to move against contact surface 36 under the action of armature rotation. When this state is reached, input 25 is to take a logic ZERO state, whereby output 27 is brought to a logic ONE level. Accordingly, transistors 29 and 32 are rendered non-conductive such that the current flow through coil 33 is interrupted. Then, the light-permeable grid system is in an opened state.

For checking the switching operation, a test switch 53 is provided which acts to simulate the function of the pair of phototransistors 1, 2. One end of switch 53 is grounded, while its other end is connected to the inputs of NAND gates 8 and 24. When the switch 53 is depressed with the grid being open, the output of gate 8 transfers to the ONE state. As for the rest, the same effect is brought about as explained above for the mode of switching of phototransistors 1, 2.

Figure 5:
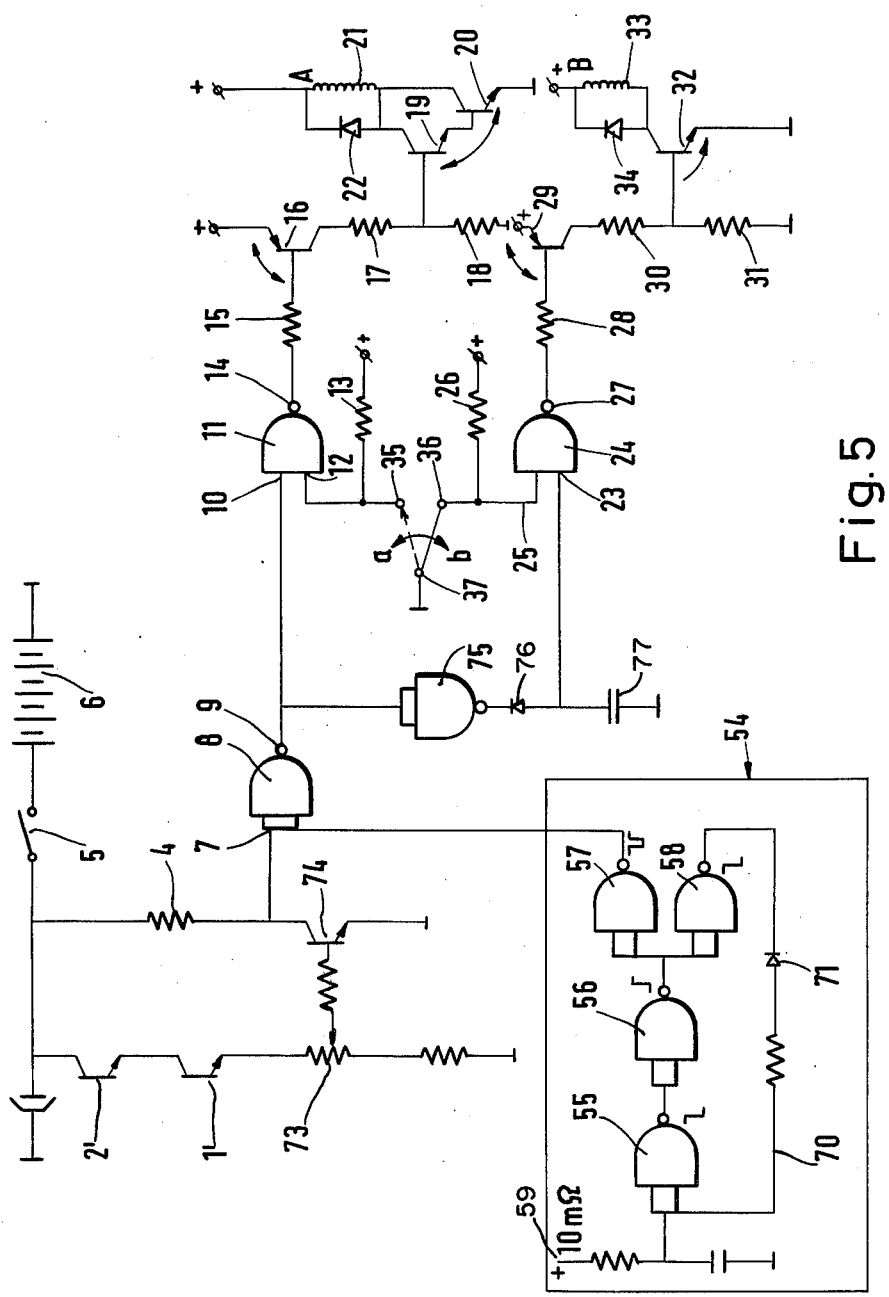
FIG. 5 is a diagram of a modified circuit for controlling the movement of the grid supports.

It has been found to be recommendable that the user of a device according to the invention is constantly given positiveness with respect to the readiness of the light-protecting function. Accordingly, it is further proposed to use, in the place of the mechanically operable test switch 53, an electronically functioning device. A device of this type is illustrated in FIG. 5. The safety circuit shown, as generally indicated at 54, fully assumes the function of test switch 53 of FIG. 3, even if FIG. 5 shows a slightly modified configuration of connection of the phototransistor input circuit. Circuit 54 comprises essentially a known per se sweep voltage generator which, as a free-running oscillator, constantly supplies the NAND gate 8 with pulses having a pulse duration of about 2 ms (microseconds). Depending on the frequency chosen, the safety circuit in this manner activates the darkening effect of the grid more or less frequently, such that the user notices that the cut-off device operates properly.

To this effect, NAND gates 55 to 58 are connected to a current source 59 in circuit 54, which current source is coupled to the input of NAND gate 55. By means of the feedback circuit 70 and of the diode 71, as indicated, switching pulses are hereby produced from stage to stage, which pulses show a square configuration at the output of gate 57. The oscillator circuit 54 need not be discussed in detail because such circuit is known per se.

In the place of the input circuit of FIG. 3 for the phototransistors, a different mode of connection has been chosen for the light-sensitive transistors (type FPT 100) according to FIG. 5. The circuit branch including transistors 2' and 1', respectively, is not directly coupled to NAND gate 8, rather, this branch is connected to the base of an npn-type transistor 74 through a potentiometer. As soon as light is incident on transistors 1' and 2', the emitter-base voltage of transistor 74 varies such that input 7 at gate 8 assumes a logic ZERO level. This initiates the above described switching operation.

The sensitivity of the light-sensitive circuit branch may be controlled by variation of the potentiometer 73, namely by reducing the potentiometer resistance between transistors 1', 2' and 73/74 (more sensitive) or by increasing such resistance (less sensitive).

The mode of functioning of the NAND gate 75, assisted by diode 76 and capacitor 77, enables, to keep the grid closed for a while, when the torch stops burning. A certain time will lapse, until a current through the resistance of diode 76 will build up a logical ONE at input 23, thereby causing the opening of the grid by solenoid 33. This results in a protection against infrared radiation, which is emitted by the hot welded object.

For adaptation to different types of light (spectra) and welding operations, the viewing window including the grids is designed to be exchangeable as a unit. In this construction, the electronic portion including the phototransistors is attached to the protective device (the protective hood in the present instance). The jaws of armature receive therebetween the lug 42 such that the hood is ready for operation again immediately upon insertion of the viewing window. Additionally, small filters may be connected to the replaceable components, which filters, when applied, slide over the phototransistors so as to vary their characteristics, too.

The regulations for the procurement of eye protection or safety glasses (Dutch H.C.N.N. Standards N 952) distinguish betweend six types of safety glasses:

A = For glass melting furnaces up to a temperature of 1,600° C.
B = For glass melting furnaces having a temperature in excess of 1,600° C.
C = For autogenous welding
D = For electric-arc welding up to 75 amperes
E = For amperages of from 75 to 200 amperes
F = For amperages in excess of 200 amperes.

Specific factors of permeability and limits are defined at various lengths of light waves. Corresponding glasses are known which provide these values. For example, if vapor-deposited silver is used as the grid strip substance, the infrared portions can easily be filtered out. In particular, it is proposed that the support and strip materials are matched to each other in such a manner that components of radiation in the fringe area of the spectrum are filtered out from the outset. Hereby, radiation within the infrared range is filtered out by the strip or coating material of the grid, whereas ultraviolet radiation is filtered out by the substrate material. On the whole, this results in a still better filtering effect and in a surprisingly advantageous utilization.

Normally a uniform distribution of grid strips is performed. But besides this distribution it will be possible to perform other kinds as well:

1. The substance of the strips varies in thickness. It will be thicker at the bottom and thinner at the top, so giving all types of absorption according to regulations mentioned above.

2. The window is divided into a lower part and an upper part. Only the lower part is constructed as a movable grid, whereas the upper part has a constant, strong light absorption factor and will be non-moveable. With such a grid, which has a low mass, the switching time will be very short.

3. The window according to type 2 is constructed, that the upper part consists of two parts, lying parallel, which can be manually adjusted relative to another. By choosing a decreasing absorption from left to right with the first window and from right to left for the second, the areas of the highest absorption are lying at the outer sides when being seen through. Areas of weak absorption are situated in the middle. When th windows are shifted to the middle and relative to one another, the absorption will increase to a maximum.

The range of shiftability are given by the width of the window and the area of view necessary. The absorption preferably will vary in the range of the regulation data (Dutch H.C.N.N. Standards) A ... F.

These variations imply substantially, that the window is constructed in two parts, whereby the upper part is set to a constant translucence, and the lower part can be opened and closed by the said circuitry.

What we claim is:

1. Automatic protective equipment for performing work in areas of greatly varying light intensities, said equipment comprising:

wall means;

a transparent window mounted at a fixed position within said wall means;

first planar filter means mounted so as to cover at least a portion of said transparent window, having uniform grid strips thereon reaching from one side of said first filter means to the opposite side, said grid strips being highly absorbent of all electromagnetic radiation incident thereon of selected frequencies, and said first filter means having elongated areas between said grid strips highly transparent to all incident visible light, said grid strips and said highly transparent areas respectively lying parallel and being of uniform width;

second planar filter means adjacent to said first filter means, covering said first filter means, and mounted for movement relative to said first filter means through a predetermined limited distance, said second filter means having uniform grid strips thereon parallel to the grid strips on said first filter means, said second filter means grid strips reaching from one side of said second filter means to the opposite side, said grid strips being highly absorbent of all electromagnetic radiation incident thereon of selected frequencies, said second filter means having elongated areas between said grid strips highly transparent to all orientations of incident visible light, the width of said second filter means grid strips being at least as great as the width of said first filter means transparent areas;

electrically energizable means attached to said wall means, having a first magnetic coil, a second magnetic coil, and an armature connected to said second filter means and magnetically flux-linked with said first and second magnetic coils for moving said second filer means in a first direction through said limited distance relative to said first filter means when said first magnetic coil is energized and for moving said second filter means in a second direction opposite said first direction through said limited distance when said second magnetic coil is energized;

spring means for urging said second filter means through said limited distance in said second direction when said first magnetic coil is de-energized and said second magnetic coil is energized, so that when said second filter means has moved said limited distance in said first direction when said first magnetic coil is energized, said grid strips and said highly transparent areas of said second filter means cover respectively said grid strips and said highly transparent areas of said first filter means, thereby forming a relatively highly transparent window area, and when said second filter means moves said limited distance in said second direction when said second magnetic coil is energized, said grid strips of said second filter means covver said highly transparent areas of said first filter means, thereby forming a highly absorbent covering for said transparent window; and controlling means for energizing said energizable means in response to incident radiation comprising:

photoelectric means responsive to incident radiation, and amplifier means, having an output connected to said energizable means and an input connected to said photoelectric means for energizing said first magnetic coil when high intensity electromagnetic radiation is incident on said photoelectric means and for energizing said second magnetic coil when low intensity electromagnetic radiation is incident on said photoelectric means, so that as said radiation changes between high and low intensity levels, said second filter means shifts in said first and second direction respectively through said limited distance, thereby prohibiting high intensity light from damaging the eyes of a user of said equipment by first heavily filtering said high intensity light with said highly absorbent grid strips on said first and second filter means.

2. Equipment as in claim 1 wherein:
said controlling means further comprises a logic control circuit having a Darlington transistor pair.

3. Equipment as in claim 1 wherein said controlling means further comprises a light-sensitive resistor positioned so that only ambient light is incident thereon, said resistor setting the sensitivity of said control means to various radiation levels.

4. Equipment as in claim 2 wherein said logic control circuit includes a test means for simulating the condition of high intensity radiation incident on said photoelectric means when said test means is in a predetermined condition.

5. Equipment as in claim 4 wherein said test means comprises an oscillator circuit, connected to said logic control circuit for causing pulses of variable intervals to be applied alternately to said first and said second magnetic coils.

6. Equipment as in claim 2 further including two magnetic yokes, each respectively positioned proximate to said first and second magnetic coils, said yokes being composed of magnetic material showing residual magnetism upon termination of the current flow through the respective one of said magnetic coils, so that said second filter means remains in the position most recently assumed.

7. Equipment as in claim 2 wherein said second magnetic coil includes a secondary winding which compensates, when energized, for the tension placed on said second filter means by said spring means.

8. Equipment as in claim 2 further comprising: two U-shaped magnetic yokes, the free legs of said yokes facing each other, each of said yokes being proximate to one of said magnetic coils;

an armature made of a ferromagnetic substance mounted between said yokes so as to be capable of moving therebetween; and coupling means for attaching said armature to said second filter means.

9. Equipment as in claim 8 wherein said equipment further comprises mounting means for said first and said second filter means; and wherein said coupling means permits said mounting means together with the mounted elements to be easily detached from said wall means and replaced by an alternate mounting means in order to provide filtering in varying operating conditions.

10. Equipment as in claim 1 wherein said grid strips filter out the invisible radiation in the fringe area of the visible light spectrum.

11. Equipment as in claim 1 wherein said grid strips conform with Electrical Welding Standards with respect to their filtering effect.

12. Equipment as in claim 1 further comprising a spacing means between said first and said second filter means for reducing the friction therebetween and eliminating the wear thereof.

13. Equipment as in claim 1 wherein the width of one said grid strip and one said translucent area pair in said first and said second filter means is less than two millimeters.

14. Equipment as in claim 1 further comprising a solar cell powered by the electromagnetic radiation resulting from welding for supplying electricity to said solenoid means and said control means.

15. Equipment as in claim 1 wherein said first and said second filter means covers only the lower portion of said transparent window; and said equipment further comprises a third filter means over the upper portion of said transparent window for providing a constant translucence while work is being performed.

16. Apparatus as in claim 15 wherein said third filter means comprises:

a first filter decreasing in absorption from left to right;

a second filter decreasing in absorption from right to left; and means for mounting said first and said second filters so as to cover said upper portion of said transparent window, so that said first and said second filters lie one behind the other, and so that at least one of said first and said second filters can be shifted manually relative to another so as to vary the translucence of said third filter means.

* * * * *